United States Patent [19]

Mittleman

[11] 4,307,869
[45] Dec. 29, 1981

[54] ONE WAY SLIDE CLAMP FOR TUBING

[75] Inventor: Herbert Mittleman, Deerfield, Ill.

[73] Assignee: Baxter Travenol Laboratories, Inc., Deerfield, Ill.

[21] Appl. No.: 216,304

[22] Filed: Dec. 15, 1980

[51] Int. Cl.³ .............................................. F16K 7/04
[52] U.S. Cl. ........................................ 251/7; 24/264; 24/130; 128/205.17
[58] Field of Search ................ 251/4, 7; 24/264, 130; 411/529; 128/205.17, 346; 29/282, 235, 450

[56] References Cited
U.S. PATENT DOCUMENTS

| D. 200,729 | 3/1965 | Coanda et al. | 251/7 |
| 2,092,400 | 9/1937 | Miller | 251/7 |
| 2,503,327 | 4/1950 | Fields | 251/7 |
| 2,889,848 | 6/1959 | Redmer | 251/7 |
| 3,247,852 | 4/1966 | Schneider | 128/346 |
| 3,316,935 | 5/1967 | Kaiser | 251/4 |
| 3,357,674 | 12/1967 | Coanda et al. | 251/7 |
| 3,374,509 | 3/1968 | Logan et al. | 251/4 |
| 4,248,401 | 2/1981 | Mittleman | 251/7 |

Primary Examiner—H. Jay Spiegel
Attorney, Agent, or Firm—John P. Kirby, Jr.; Kirk McInerney; Bradford R. L. Price

[57] ABSTRACT

A one-way slide clamp is provided having a slot member with a one-way passageway intermediate a tube receiving section and a tube crimping section to restrain the tubing in the crimping section thereby permanently sealing the fluid passageway.

9 Claims, 6 Drawing Figures

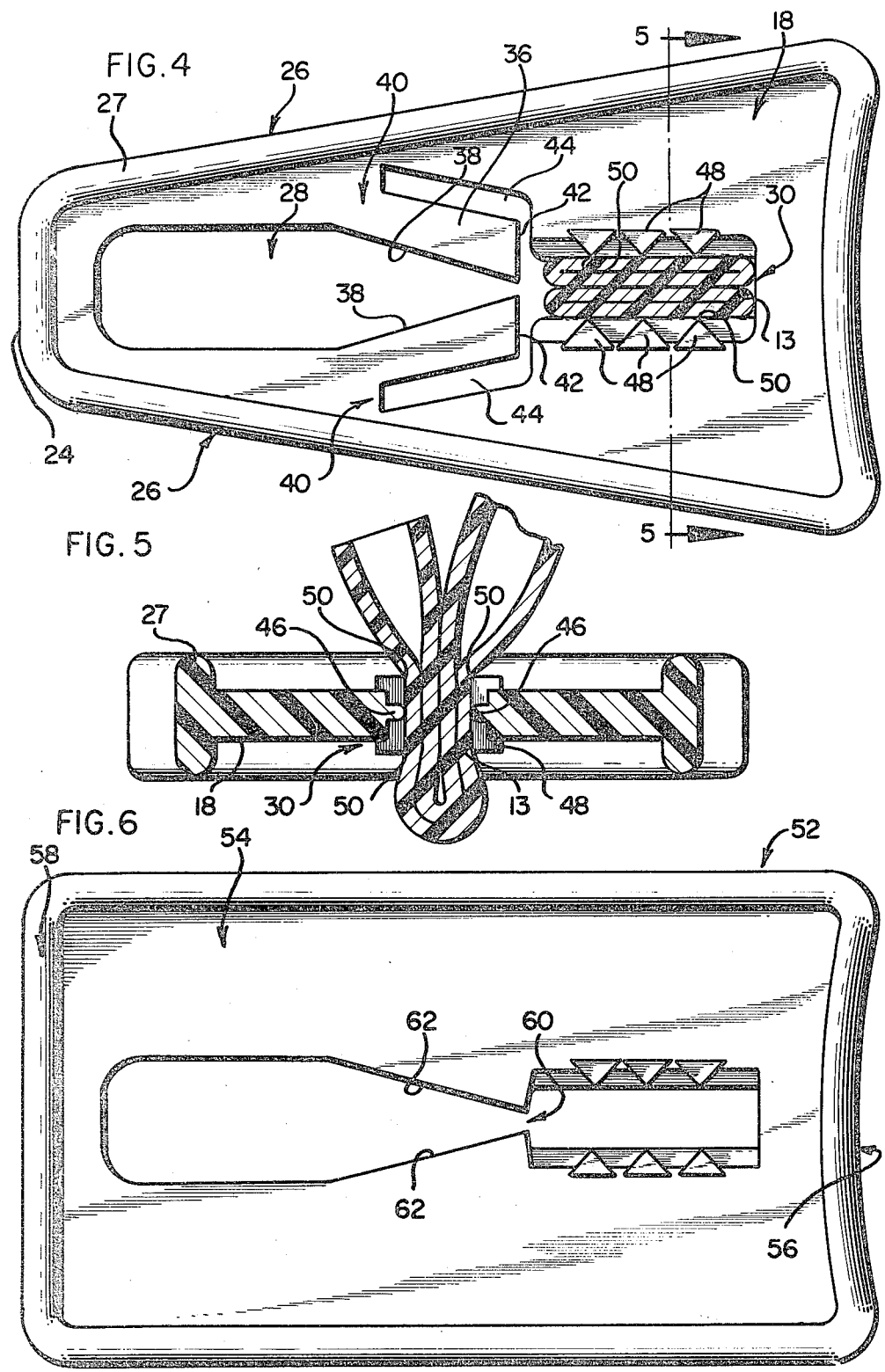

ONE WAY SLIDE CLAMP FOR TUBING

BACKGROUND OF THE INVENTION

The present invention relates generally to tubing clamps and particularly to a one-way slide clamp which is employed to close and seal the fluid passageway of flexible tubing. Several types of slide clamps, which are principally employed in hospital and medical applications, have been proposed in the prior art. Those slide clamps are designed to permit an operator to repeatedly open and close the fluid passageway of tubing by manipulating the clamp back and forth. A potentially serious drawback of the reversable on-off slide clamps in general is that a patient may intentionally or unintentionally tamper with the device causing a potentially dangerous change in the desired fluid flow unbeknownst to the nurse or operator. Generally, those reversable slide clamps have not been employed for applications requiring that a section of fluid tubing be permanently sealed.

For example, one such application includes parenteral solution containers which are supplied either empty or partially filled permitting a physician or hospital personnel to transfer or admix a prepared parenteral solution through an entry port into the container. After the container has been filled with the desired solution, it is necessary to hermetically and permanently seal the inlet tubing.

One method of sealing the inlet tube after the desired solution has been admixed includes a pliable, metal collar which is crimped over the inlet tubing by a pair of specialized pliers. Another method for sealing the inlet tube includes melting the tube together by means of a heat sealing apparatus. Although these methods do seal the tubing, both require additional specialized tools or devices which are expensive and oftentimes are not readily available, causing an inconvenience to the hospital personnel. Moreover, metal collars absorb heat and microwave radiation, often employed to thaw the solution ater a period of storing the container in a freezer. The metal collar heats and can melt a hole in the inlet tube, ruining the container and its prepared solution.

The need exists for a one-way slide clamp which is readily employed to seal the fluid tubing and is easily applied by hospital personnel to thereafter maintain a tamper-proof and sterile seal.

SUMMARY OF THE INVENTION

An object of the present invention is to provide a one-way clamp or tubing to permanently close and seal the fluid passageway of plastic tubing.

An additional object of the present invention is to provide a one-way slide clamp fabricated from a material which does not absorb microwave radiation and which is readily manipulable by the user to hermetically seal plastic tubing and is restrained from returning to an unsealed position.

A further object is to provide a disposable, a plastic one-way slide clamp for hermetically sealing plastic tubing within a crimping slot without the danger of the seal being broken by further intentional or unintentional manipulation of the clamp.

BRIEF DESCRIPTON OF THE FIGURES

The above and other objects of the invention are more particularly set forth in the following detailed description and in the accompanying drawings of which:

FIG. 4 is a plan view of the embodiments shown in FIGS. 2 and 3 with the tubing in the sealed position;

FIG. 5 is a sectional view of FIG. 4 taken along line 5—5;

FIG. 6 is a plan view of another embodiment of the invention.

DESCRIPTION OF THE PREFERRED EMBODIMENT

The present invention provides for a slide clamp which is adapted to close and thereafter seal the fluid passageway of tubing, particularly plastic tubing employed in hospitals and plastic inlet tubing employed for transferring parenteral solutions into a container. Plastic tubing is extensively used in medical applications as a fluid conduit between a container at one end and a patient, or for transferring fluids from one container to another. The present invention provides a one-way slide clamp which can be employed to permanently and hermetically seal the fluid conduit of tubing in a facile and tamper-proof manner.

Figure 1:
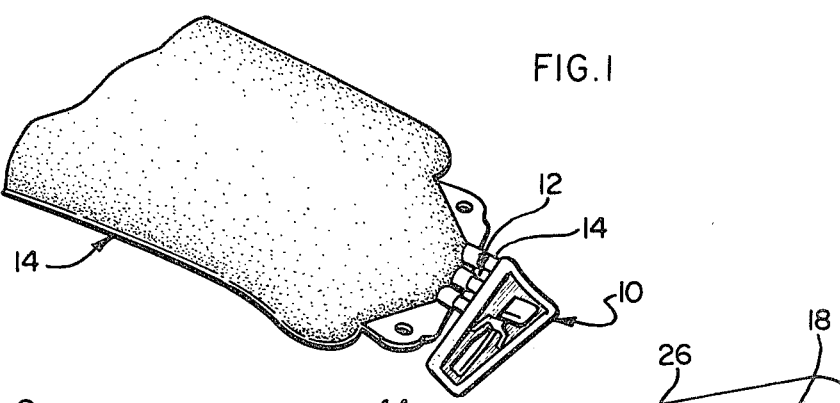
FIG. 1 is a perspective view of an embodiment of the invention shown in one application to seal the inlet tubing of a parenteral solution container.

Referring now to FIG. 1, a one-way slide clamp 10 is shown in use to seal an inlet port 12 of a plastic parenteral solution container or bag 14. The bag 14 contains a custom mixed solution which has been introduced from a separate container (not shown) through a length of tubing prior to being severed near the bag 14 and sealed with the clamp 10. The filled bag 14 may be stored for extended period, at low or freezing temperatures, until needed for a particular patient. When needed, the bag is removed from storage and is preferably heated to about body temperature in a low intensity microwave oven. Thereafter, the bag 14 is supported, usually in an inverted position, during administration of the solution to a patient through a suitable administration port 16.

Figure 2:
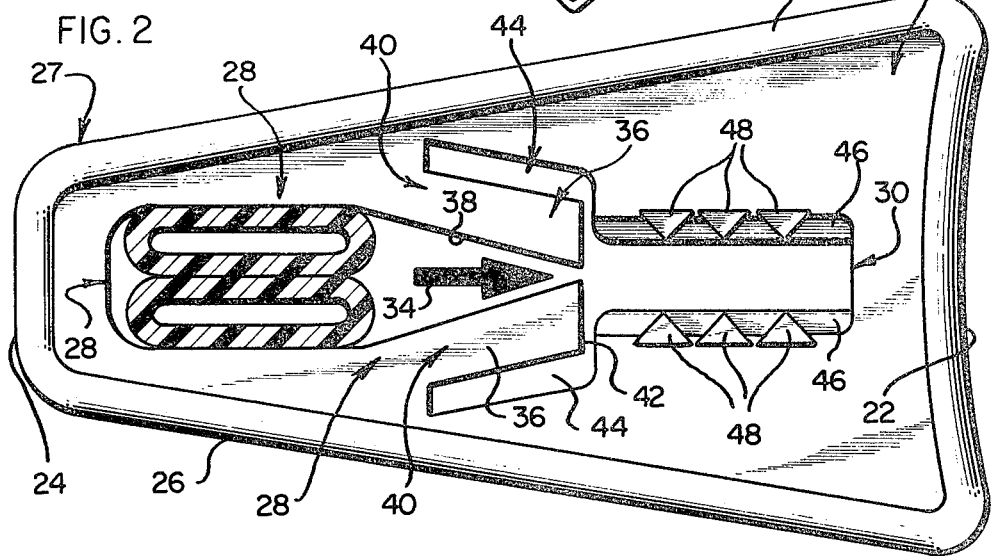
FIG. 2 is plan view of an embodiment of the invention with a piece of tubing shown in an unsealed, folded configuration.
Figure 3:
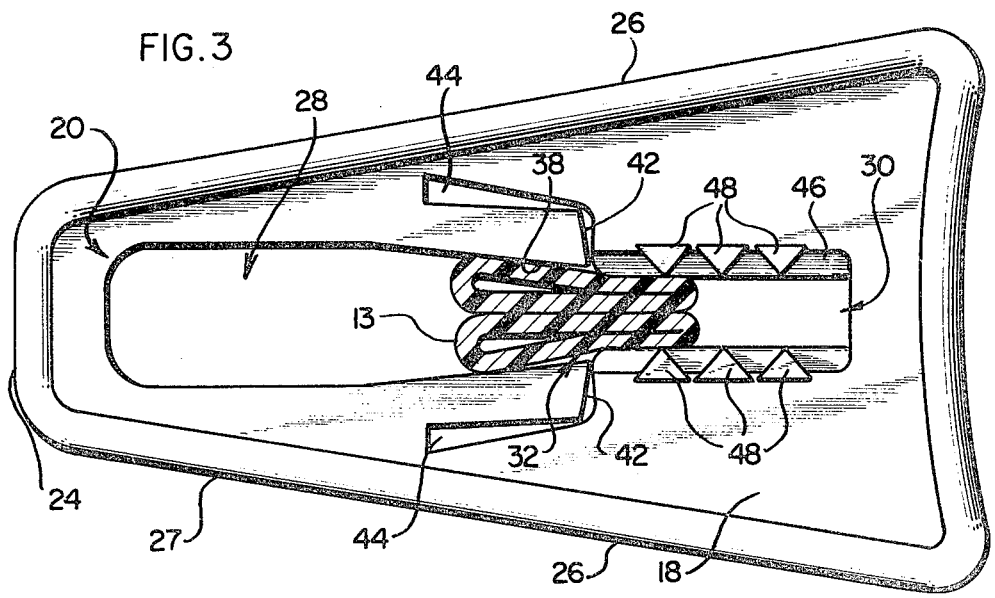
FIG. 3 is a plan view of the embodiment as shown in FIG. 2 depicting the tubing as it would appear during longitudinal movement to a sealed position.

FIGS. 2, 3 and 4, illustrate the structure and operation of the clamp 10 embodying various aspects of the invention in use with the inlet tubing 12 which has been doubled over into a folded section 13. The clamp 10 includes an elongated body 18 with a slot member 20 disposed through the body 18. As shown, the body 18 is shaped like a truncated triangle having a contoured transverse end 22 and a smaller transverse end 24 with two longitudinal sides 26. The clamp 10 is illustrated with an optional peripheral border 27 of slightly greater thickness than the body 18.

The slot member 20 consists generally of a receiving section 28 and a crimping section 30 which are longitudinally connected by a one-way means such as a passageway 32. The one-way passageway 32 includes at least one, and preferably two spring fingers 36 which define two side walls 38 of the passageway 32. The spring fingers 36 are integral with the clamp body 18 at their base ends 40 and transversely pivotable at their ends 42. The fingers 36 and ends 42 transversely pivot into a suitably dimensioned unobstructed space 44 in the body 18 along the finger 36 opposite to the side wall 38. As shown, the fingers 36 are oriented so that in an unexpanded or neutral position, the side walls 38 converge from a transverse spacing approximately equal to that of the receiving section 28 at their base 40 to a transverse spacing which is less than that of the crimping section 30, thereby leaving the free ends 42 partially obstructing the crimping section 30.

As generally depicted in FIGS. 1 and 2, the receiving section 28 of the slot 20 is preferably dimensioned to readily receive and loosely restrain the folded tubing 13. More specifically, when the transfer of the parenteral solution through the tubing 12 into the bag 14 is completed, the operator folds over the tubing with one hand and readily inserts the folded portion 13 into the receiving section 28 of the slot. The receiving section 28 is appropriately dimensioned to loosely receive a particular size of tubing, preferably to receive a folded section of tubing, in order to retain the clamp and tubing in this position until the operator seals the tubing in the crimping section 30. The tubing 13 is positioned and sealed in the crimping section 30 by applying thumb pressure to the end 22. Arrow 34 in FIG. 2 depicts the direction that the tubing 13 travels from the receiving section 28 through the one-way passageway 32 into the crimping section 30.

The tubing 13 is longitudinally moved through the passageway 32 between the side walls 38 of the spring fingers 36. As shown in FIG. 3, the spring fingers 36 and their ends 42 are transversely expanded into the spaces 44 as the tubing 13 is partially compressed by the inward tension of the side walls 38 facilitating passage of the tubing into the crimping section 30.

As sequentially shown in FIGS. 3 and 4, continued movement positions the tubing 13 completely into the crimping section 30. The resiliency of the spring fingers 36 inwardly returns their free ends 42 to the unexpanded position adjacent to and having a transverse spacing less than that of the crimping section 30 as shown in FIG. 4. The ends 42 of the spring fingers 36 prevent the tubing 13 from being moved in the opposite direction out of the crimping section 30. Accordingly, the tubing remains sealed within the crimping section 30 in a tamper-proof manner.

The crimping section 30, as shown in FIG. 5, preferably includes contoured crimping rails 46 of substantially less thickness than the body 18 to crimp the tubing 13. Preferably, two serrated members 47 are provided longitudinally adjacent to the crimping section 30 to individually provide a series of triangularly shaped teeth 48 originating perpendicularly from the body 18 and extending to a point contiguous with the crimping surfaces 46. The teeth 48 maintain the crimped tubing 13 in a substantially perpendicular orientation to the body 18 to insure that the seal of the tubing is maintained. As shown, the teeth 48 are preferably thicker than the body 18 to vertically extend slightly above and below the crimping slot 18 and surfaces 46. As shown in FIG. 5, the teeth 48 have edges 50 which prevent the crimped tubing 13 from being perpendicularly pulled out of the section 30 by the gripping action of the edges 50 against the outwardly bowed tubing above and below the section 30.

Turning now to a particular field of operation for the present invention, when the clamp 10 is employed to seal a fluid transfer tubing for a parenteral solution bag 14 as shown in FIG. 1, the tubing is preferably doubled over or folded as is generally shown. When the transfer of the solution into the bag 14 is completed, the operator can conveniently fold the tubing forming a crease and insert the creased end into the receiving section. Creasing the tubing forms an air space to eliminate bacteria migration through any stagnant solution and insures that the crimped tubing will be hermetically sealed when positioned in the crimping section.

The slot member and clamp may be readily fabricated with appropriate dimensions to seal a folded section of tubing or to seal an unfolded or single transverse portion of the tubing.

In addition to the hermetic sealing advantages of a clamp dimensioned for a folded section of tubing, the dimensional tolerances for the receiving and crimping sections, and the passageway of the slot member are not as critical as would be required for sealing a single transverse section of tubing. In this regard, the transverse spacing of the crimping slot can acceptably vary between the range of about 20% to about 45% less than the thickness of the tubing wall multiplied by four. Moreover, a folded section of tubing reduces the criticality of the transverse dimensions between the ends of the spring fingers in their neutral position, which is preferably on the order of about one-eighth that of the transverse width of the crimping slot.

As shown in FIG. 6, the clamp 52 may be fabricated with a rectangular body 54. The body 54 is provided with a contoured transverse end 56 and a straight end 58 to insure that an operator does not unknowingly attempt to remove the clamp 52 after it has sealed a piece of tubing. Additionally, the expansion area and the resilient spring arms have been replaced by a one-way passageway 60 integral with the body 54. The passageway 60 is appropriately dimensioned in a fixed configuration by side walls 62 which converge to a transverse spacing which readily allows the tubing to pass therethrough, but is sufficiently less than the crimping slot to prevent the reverse movement of the tubing once positioned in the crimping slot to maintain the crimped position of the clamp.

The one-way clamp of the present invention is readily fabricated by known injection molding techniques with numerous injection moldable plastic materials and is preferably molded from plastic materials having properties and colors which do not absorb microwave radiation.

Although the invention has been described in terms of preferred structures, it will be apparent to one skilled in the art that obvious modifications may be made without departing from the invention. It is intended that all such modifications are included in the spirit and scope of the invention as defined herein and protected by the appended claims.

What is claimed is:

1. A slide clamp for tubing having a fluid passageway comprising:
    an elongated body having a longitudinal length and transvers width;
    a slot member disposed within said body having a receiving section and a crimping section, said receiving section being dimensioned to loosely restrain the tubing and said crimping section being dimensioned to crimp shut the fluid passageway; and
    one-way means intermediate said receiving and said crimping sections for allowing longitudinal movement of the tubing from the receiving section to the crimping section and for thereafter preventing longitudinal movement of the crimped tubing from the crimping section, whereby the clamp is loosely held in place with the tubing positioned within the receiving section until an operator longitudinally positions and seals the tubing in the crimping section.

2. The slide clamp of claim 1 wherein the one-way means includes a passageway longitudinally joining the receiving and crimping sections of the slot member, said passageway including an interface and having at least one side wall which tapers inwardly from said receiving section to define, at the interface between the sections, a transverse width less than the crimping section.

3. The slide clamp of claim 2 wherein at least one side wall is a transversely pivotable spring finger so as to transversely flex during longitudinal movement of the tubing through the passageway towards the crimping slot and thereafter return to an unflexed position to retain the tubing in the crimping slot.

4. The slide clamp of claim 2 wherein the slot member is dimensioned to receive and to crimp a folded section of tubing and the transverse width of the passageway at said interface with the crimping section is about one-eighth the transverse width of the crimping section.

5. The slide clamp of claims 2 or 4 wherein the transverse width of the crimping section is about twenty percent to about forty-five percent of four times the width of a wall thickness for the tubing.

6. The slide clamp of claim 3 wherein the passageway includes two side walls each having a transversely pivotable spring finger so as to transversely flex during longitudinal movement of the tubing through the passageway towards the crimping slot and thereafter return to an unflexed position to retain the tubing in the crimping slot.

7. The slide clamp of claim 1 wherein the crimping section of the slot member further includes:
  rounded crimping surfaces projecting inwardly from the crimping section having a thickness less than the body; and
  means for maintaining the crimped tubing substantially perpendicular with respect to the crimping section so as to maintain a hermetic seal and for gripping the tubing to prevent the tubing from being pulled out of the crimping section.

8. The slide clamp of claim 7 wherein the maintaining and gripping means further includes:
  two, inwardly serrated members adjacent the crimping section, said members having a thickness greater than the thickness of the contoured crimping surfaces.

9. The slide clamp of claim 8 wherein the serrated members have a thickness greater than the thickness of the body.

* * * * *